United States Patent [19]
Huerlimann et al.

[11] Patent Number: 5,099,679
[45] Date of Patent: Mar. 31, 1992

[54] MEASUREMENT OF OXYGEN AND RESIDUAL PRESSURE OF A PACKAGE

[75] Inventors: Peter Huerlimann, Konolfingen; Eugéne Van Meir, Fribourg, both of Switzerland

[73] Assignee: Nestec S.A., Vevey, Switzerland

[21] Appl. No.: 584,250

[22] Filed: Sep. 18, 1990

[30] Foreign Application Priority Data

Oct. 9, 1989 [EP] European Pat. Off. ........ 89118744.5

[51] Int. Cl.⁵ .................. G01N 7/14; G01D 21/02
[52] U.S. Cl. .................. 73/19.06; 73/31.04; 73/52
[58] Field of Search .......... 73/31.04, 19.05, 19.06, 73/52, 864.74

[56] References Cited

U.S. PATENT DOCUMENTS

| | | | |
|---|---|---|---|
| 3,201,994 | 8/1965 | Adams | 73/864.74 X |
| 3,203,248 | 8/1965 | Stutler et al. | 73/864.74 X |
| 3,374,678 | 3/1968 | McGuckin | 73/864.74 X |
| 3,849,020 | 11/1974 | Garza et al. | |
| 4,133,736 | 1/1979 | Nakagawa et al. | |
| 4,733,555 | 3/1988 | Franks | 73/52 X |
| 4,926,681 | 5/1990 | Fitzpatrick | 73/19.06 X |

FOREIGN PATENT DOCUMENTS

| | | |
|---|---|---|
| 3439778 | 4/1986 | Fed. Rep. of Germany . |
| 3505490 | 8/1986 | Fed. Rep. of Germany . |
| 267169 | 7/1970 | U.S.S.R. ................ 73/52 |

Primary Examiner—Hezron E. Williams
Assistant Examiner—Joseph W. Roskos
Attorney, Agent, or Firm—Vogt & O'Donnell

[57] ABSTRACT

Residual pressure and oxygen content of a pack are measured in an apparatus having a pressure measuring system and an oxygen measuring system in a branched arrangement. The oxygen content is measured by employing a vacuum pump to displace gas from the pack to an oxygen measuring system and a compression chamber which is then reset to atmosperic pressure and the oxygen content of the gas is measured. A two-way valve enables stopping displacement of the gas to the oxygen measuring system and enables the oxygen measuring system and compression chamber to be reset to atmospheric pressure.

16 Claims, 1 Drawing Sheet

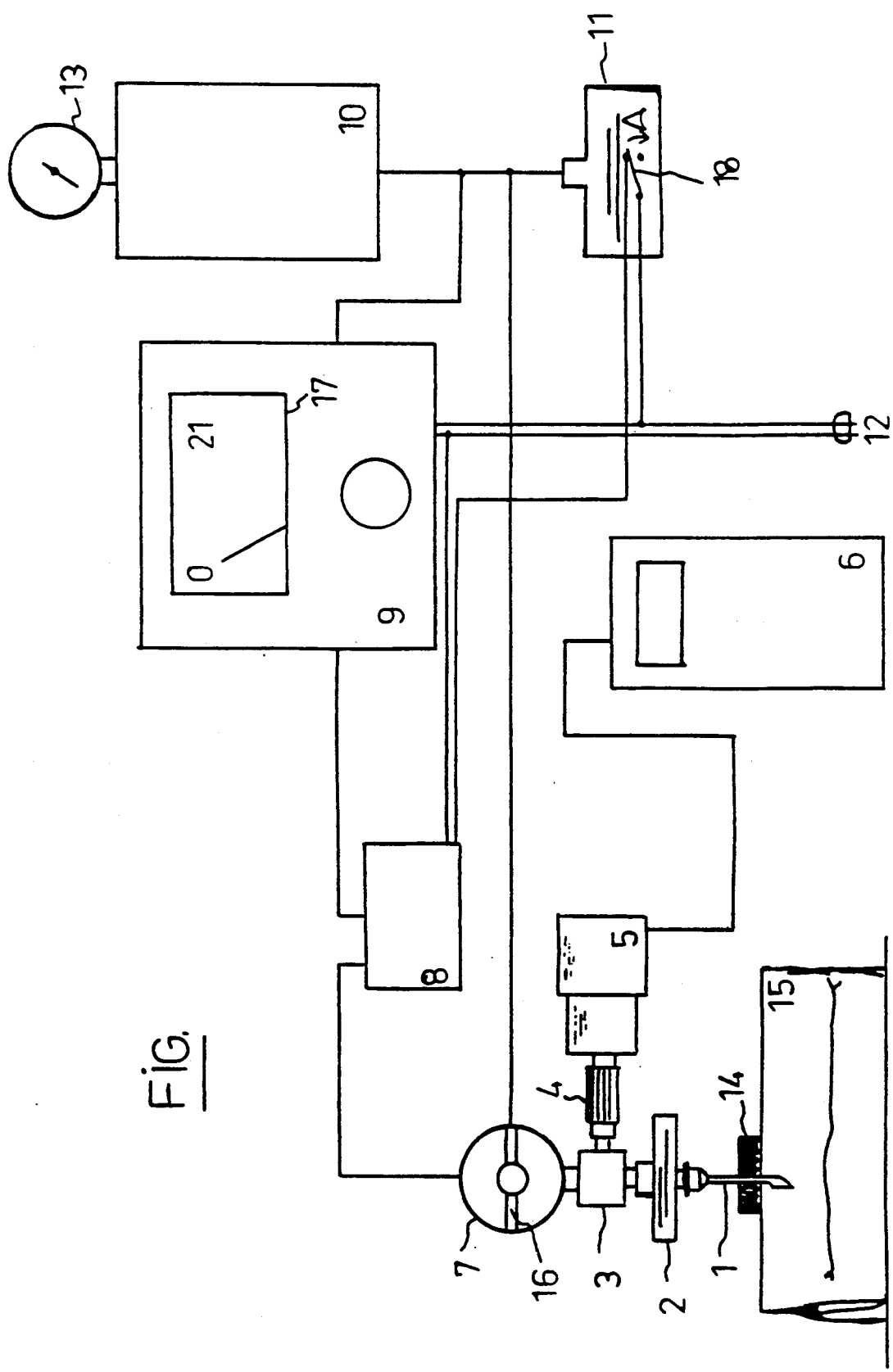

MEASUREMENT OF OXYGEN AND RESIDUAL PRESSURE OF A PACKAGE

BACKGROUND OF THE INVENTION

This invention relates to a process for the simultaneous determination of the oxygen content and the residual pressure of a pack. The invention also relates to an apparatus for carrying out this process.

DE-OS 34 39 778 relates to an apparatus for measuring the pressure and the oxygen content in a sample. However, this apparatus is relatively complicated, operates in vacuo and does not guarantee exact measurement because it is not known whether a sufficient quantity of gas has been introduced into the measuring system, in addition to which it can lead to the obstruction of pipes through the entry of powder.

The process and apparatus according to the invention enables these disadvantages to be obviated. The apparatus according to the invention is relatively simple, easy to handle, operates at atmospheric pressure and always guarantees that a sufficient volume of gas has been displaced from the pack to allow exact measurement.

SUMMARY OF THE INVENTION

The present invention relates to a process and apparatus for the simultaneous determination of the oxygen content and the residual pressure in a pack in which the pressure in the pack is measured with a means for removing gas and the oxygen content is measured downstream of said means and a two-way valve by displacement of the residual gas into an oxygen measuring system followed by a compression chamber which are reset to atmospheric pressure by said valve during said measurement.

In the context of the invention, a pack is understood to be any type of pack, both flexible and rigid, such as bags, cans or glass packs. The packs may contain both powders and liquids. These packs may be under a vacuum or at atmospheric pressure, for example for packing milk powders, cereals, coffee and the like. A vacuum pack is understood to be a pack in which the absolute pressure is at least 250 mbar.

The advantage of the process and apparatus according to the invention is that it enables the two above-mentioned measurements to be carried out very rapidly, with considerable reliability and with a good guarantee in regard to the oxygen content observed.

DETAILED DESCRIPTION OF THE INVENTION

The object of the process is to ensure that sufficient gas has been displaced from the pack to have the exact value of the oxygen content. To this end, a slight excess pressure of at most 100 mbar is established in the compression chamber and the measurement is then carried out by return to atmospheric pressure.

This minimum value of 100 mbar in excess of atmospheric pressure is determined in advance, and the volume of the compression chamber which enables the exact value of the oxygen content to be given is then determined.

The apparatus for carrying out the process of the present invention comprises a means for removing gas, a pressure sensor and a pressure measuring system in a branched arrangement and, downstream of the means for removing gas, a two-way valve, a vacuum pump for displacing the residual gas from the pack, an oxygen measuring system and a compression chamber connected to the two-way valve for resetting to atmospheric pressure.

The means for removing gas is in the form of a hollow needle, which merely has to be inserted into a pack during the measurement by which residual gas can be withdrawn from the pack under suction with the support of the vacuum pump.

The compression chamber comprises a manometer for measuring therein the minimum excess pressure required to guarantee a sufficient displacement of gas from the pack to ensure the accuracy of the measurement of the oxygen content. The vacuum pump used is a membrane pump because it has a very small dead volume so that measurement of the oxygen content is not in any danger of falsification.

The volume of the compression chamber is defined by the maximum excess pressure which can be tolerated in the measuring system and by the minimum quantity of gas to be displaced to obtain exact results. The volume is advantageously between 0.2 and 0.8 liter and preferably of the order of 0.3 to 0.4 liter.

The apparatus according to the invention is designed for the measurement both of flexible vacuum packs and of cans containing milk powder or coffee extract. In this case, to prevent powder entering the apparatus, a filter is provided between the means for removing gas and the two-way valve.

The oxygen measuring system is sensitive to excess pressures. Accordingly, a safety switch is provided between the vacuum pump and the compression chamber. This switch cuts off the vacuum pump when the manometer of the compression chamber indicates an excess pressure of approximately 100 mbar.

The invention is described in more detail in the following with reference to the accompanying drawing which illustrates the apparatus according to the invention.

BRIEF DESCRIPTION OF THE DRAWING

The accompanying Drawing FIGURE schematically depicts the elements of the present invention further described below.

DETAILED DESCRIPTION OF THE DRAWING

The apparatus comprises a hollow needle (1) connected to a filter (2) and to a coupling (3). In a branched arrangement, there is a connection (4), a pressure sensor (5) and a pressure measuring system (6). The two-way valve (7) is arranged between the coupling (3) and the vacuum pump (8). Downstream of the pump is the oxygen measuring system (9) and the compression chamber (10) comprising a manometer (13) and the safety switch (11). The elements (8), (9) and (11) are connected to the power supply.

Before the apparatus according to the invention is brought into operation, the oxygen measuring system (9) has to be calibrated. To this end, the pump (8) is switched on, the needle (1) is connected to a source of nitrogen and the valve (7) is placed in the vertical position. After a few seconds, when the manometer (13) indicates 80 mbar, the system is reset to atmospheric pressure and the O is adjusted on (9). Since air contains 21% oxygen, the previous operation is repeated leaving the needle (1) in the open air. When the manometer (13) indicates 80 mbar, the valve (7) is moved into the horizontal position and the needle is adjusted to 21 on (9).

On the other hand, it is known that, with a volume of the compression chamber of 0.35 liter, as used, an excess pressure of approximately 80 mbar in said chamber enables an exact value of the oxygen content in the pack in question to be given.

To carry out an actual measurement, the needle (1) is raised and a pack (15)—to which a piece of foam (14) is bonded to establish fluid tightness—is placed beneath the needle. The vacuum pump (8) having already been switched on and the valve (7) being in the position illustrated, the needle is lowered to pierce the pack (15) and the pressure is read off from the pressure measuring system (6). The valve (7) is then opened and the vacuum pump (8) displaces the residual gas towards the oxygen measuring system (9). When the manometer (13) indicates 80 mbar, the valve (7) is returned to the position illustrated to stop the displacement of residual gas from the pack and to restore atmospheric pressure in the oxygen measuring system and compression chamber. The value of the oxygen content is then read off from the scale (17) of the measuring system (9).

If an excess pressure of 100 mbar is exceeded in the chamber (10), the contactor (18) of the switch (11) is moved in the direction of arrow A and the pump stops because the electrical current is cut off. The oxygen measuring system may be a device of the HELANTEC or SERVOMEX type. The pressure measuring system is, for example, a device of the KELLER type.

The invention thus provides a simple, highly efficient, fast and reliable apparatus which operates at atmospheric pressure and which may be installed in a production line for periodically monitoring certain packs.

We claim:

1. A process for measuring residual pressure and oxygen content of a pack comprising piercing a pack with means to enable removing gas from the pack into an apparatus having a pressure measuring system and an oxygen measuring system, measuring a pressure with the pressure measuring system, displacing the gas from the pack to the oxygen measuring system which is connected to a compression chamber and establishing a pressure in the oxygen measuring system and compression chamber of up to 100 mbar in excess of atmospheric pressure and then bringing the oxygen measuring system and compression chamber to atmospheric pressure and measuring the oxygen content of the gas in the oxygen measuring system.

2. A process according to claim 1 wherein a pressure up to 80 mbar in excess of atmospheric pressure is established in the compression chamber.

3. A process according to claim 1 wherein the compression chamber has a volume of from 0.2 liter to 0.8 liter.

4. A process according to claim 1 wherein the compression chamber has a volume of from 0.3 liter to 0.4 liter.

5. A process according to claim 1 further comprising calibrating the oxygen measuring system prior to piercing the package.

6. A process according to claim 1 wherein the gas is displaced from the pack by a vacuum pump.

7. A process according to claim 6 wherein the vacuum pump is a membrane pump.

8. A process according to claim 1 wherein the piercing means is a hollow needle.

9. An apparatus for measuring oxygen content and residual pressure of a pack comprising:
   an oxygen measuring system;
   a compression chamber having a connection to the oxygen measuring system;
   means for piercing a pack for enabling removal of gas from the pack;
   a vacuum pump having a connection to the oxygen measuring system for displacing gas from the pack to the oxygen measuring system;
   a two-way valve having a connection to the piercing means and a connection to the vacuum pump for enabling the vacuum pump to displace gas via the piercing means to the oxygen measuring system and having a separate connection to the compression chamber for stopping displacement of the gas and for enabling the oxygen measuring system and compression chamber to be set to atmospheric pressure;
   a pressure sensor having a branched connection positioned between the two-way valve and the piercing means; and
   a pressure measuring system connected to the pressure sensor.

10. An apparatus according to claim 9 wherein the compression chamber has a volume of from 0.2 liter to 0.8 liter.

11. An apparatus according to claim 9 wherein the compression chamber has a volume of from 0.3 liter to 0.4 liter.

12. An apparatus according to claim 9 wherein the vacuum pump is a membrane pump.

13. An apparatus according to claim 9 wherein the means for removing gas is a hollow needle.

14. An apparatus according to claim 9 further comprising a filter for filtering gas displaced from the piercing means.

15. An apparatus according to claim 9 further comprising a safety switch for cutting off the vacuum pump when at compression chamber has a pressure of 100 mbar in excess of atmospheric pressure.

16. An apparatus according to claim 9 wherein the compression chamber is connected to a manometer for measuring pressure.

* * * * *

UNITED STATES PATENT AND TRADEMARK OFFICE
CERTIFICATE OF CORRECTION

PATENT NO. : 5,099,679

DATED : March 31, 1992

INVENTOR(S) : Peter HUERLIMANN, et al.

It is certified that error appears in the above-identified patent and that said Letters Patent is hereby corrected as shown below:

Column 4, line 52 (line 3 of claim 15), "at" should be --the--.

Signed and Sealed this

Twenty-first Day of September, 1993

Attest:

BRUCE LEHMAN

Attesting Officer

Commissioner of Patents and Trademarks